(12) United States Patent
Roach

(10) Patent No.: US 11,644,431 B2
(45) Date of Patent: May 9, 2023

(54) X-RAY FLUORESENCE APPARATUS FOR A MEASUREMENT OF MINERAL SLURRIES

(71) Applicant: MICROTRACE PTY LIMITED, Bonnet Bay (AU)

(72) Inventor: Gregory John Roach, Bonnet Bay (AU)

(73) Assignee: Microtrace Pty Limited, Bonnet Bay (AU)

( * ) Notice: Subject to any disclaimer, the term of this patent is extended or adjusted under 35 U.S.C. 154(b) by 160 days.

(21) Appl. No.: 17/268,922

(22) PCT Filed: Aug. 15, 2019

(86) PCT No.: PCT/AU2019/050852
§ 371 (c)(1),
(2) Date: Feb. 16, 2021

(87) PCT Pub. No.: WO2020/034002
PCT Pub. Date: Feb. 20, 2020

(65) Prior Publication Data
US 2021/0310969 A1 Oct. 7, 2021

(30) Foreign Application Priority Data
Aug. 17, 2018 (AU) .................. 2018903029

(51) Int. Cl.
*G01N 23/223* (2006.01)
*G01N 33/24* (2006.01)

(52) U.S. Cl.
CPC .......... *G01N 23/223* (2013.01); *G01N 33/24* (2013.01); *G01N 2223/076* (2013.01);
(Continued)

(58) Field of Classification Search
CPC ................ G01N 23/22; G01N 23/223; G01N 2223/076; G01N 2223/313;
(Continued)

(56) References Cited

U.S. PATENT DOCUMENTS

| 4,388,530 A | * | 6/1983 | Lubecki | ............... G01N 23/223 378/45 |
| 4,450,576 A | | 5/1984 | Lubecki et al. | |

(Continued)

FOREIGN PATENT DOCUMENTS

WO 2015200060 6/2015

OTHER PUBLICATIONS

Application No. PCT/AU2019/050852 International Search Report dated Sep. 10, 2019.
(Continued)

*Primary Examiner* — Allen C. Ho
(74) *Attorney, Agent, or Firm* — Keller Preece PLLC

(57) ABSTRACT

Disclosed is a measurement probe for a measurement of elements in a mineral slurry. The measurement probe includes a housing having an X-ray window. The housing encloses: an X ray source positioned to emit source X-rays at the X-ray window; an X-ray detector positioned to detect X-rays from the X-ray window; and a control module. The control module is configured to: control an operation of the X-ray source and the X-ray detector; process X-rays detected by the X-ray detector to generate X-ray spectra data; and process the X-ray spectra data to determine a quantity of one or more elements of interest in the mineral slurry. The measurement probe further includes a probe mount adapted to couple the measurement probe to a pipe mount on a pipe carrying the mineral slurry; when the probe
(Continued)

mount is coupled to the pipe mount, the X-ray window provides a transmission window for X-rays into a lumen of the pipe.

15 Claims, 4 Drawing Sheets

(52) U.S. Cl.
CPC . *G01N 2223/313* (2013.01); *G01N 2223/316* (2013.01); *G01N 2223/317* (2013.01); *G01N 2223/507* (2013.01); *G01N 2223/616* (2013.01)

(58) Field of Classification Search
CPC ....... G01N 2223/316; G01N 2223/317; G01N 2223/507; G01N 2223/616; G01N 2223/628; G01N 2223/639
USPC .................. 378/44–50, 147–151, 156–159
See application file for complete search history.

(56) References Cited

U.S. PATENT DOCUMENTS

| | | | |
|---|---|---|---|
| 4,916,719 A | 4/1990 | Kawatra et al. | |
| 5,712,891 A * | 1/1998 | Benony | G01N 23/223 378/45 |
| 5,818,899 A | 10/1998 | Connoly et al. | |
| 5,982,847 A | 11/1999 | Nelson | |
| 6,012,325 A * | 1/2000 | Ma | G01N 15/0618 73/24.02 |
| 6,233,307 B1 * | 5/2001 | Golenhofen | G01N 23/223 714/E11.21 |
| 6,266,390 B1 * | 7/2001 | Sommer, Jr. | G01N 23/223 378/45 |
| 6,295,333 B1 * | 9/2001 | Tamura | G01N 23/223 378/50 |
| 6,337,897 B1 * | 1/2002 | Kawahara | G21K 1/02 378/45 |
| 7,424,093 B2 * | 9/2008 | Fukai | G01N 23/223 378/208 |
| 7,436,926 B2 * | 10/2008 | Matoba | G01N 23/223 378/45 |
| 7,474,730 B2 * | 1/2009 | Puusaari | G01N 23/223 378/207 |
| 7,587,025 B2 * | 9/2009 | Fukai | G01N 23/223 378/86 |
| 7,627,088 B2 * | 12/2009 | Matoba | H01J 35/186 378/45 |
| 7,634,053 B2 * | 12/2009 | Matoba | G01N 23/223 378/47 |
| 7,634,054 B2 * | 12/2009 | Matoba | H01J 35/186 378/46 |
| 7,680,248 B2 * | 3/2010 | Matoba | H01J 35/186 378/140 |
| 7,796,726 B1 * | 9/2010 | Gendreau | G01N 23/20 378/80 |
| 7,916,834 B2 * | 3/2011 | Piorek | G01N 23/223 378/102 |
| 8,064,570 B2 * | 11/2011 | Tannian | G01N 23/223 378/45 |
| 8,431,357 B2 * | 4/2013 | Birnbaum | G01N 23/223 436/172 |
| 8,494,113 B2 * | 7/2013 | Grodzins | G01T 1/00 378/45 |
| 8,550,710 B2 * | 10/2013 | Kishida | G01N 23/223 378/45 |
| 8,982,338 B2 * | 3/2015 | Hamilton | G01N 21/85 356/72 |
| 9,036,778 B2 * | 5/2015 | Olszewski | G01N 23/2206 378/50 |
| 9,057,685 B2 * | 6/2015 | Allen | H01J 35/16 |
| 9,070,530 B2 * | 6/2015 | Sipilä | H01J 35/108 |
| 9,176,080 B2 * | 11/2015 | Drummy | G01N 23/223 |
| 9,683,952 B2 * | 6/2017 | Shields | G01N 23/223 |
| 9,689,815 B2 * | 6/2017 | Jones | G01N 23/223 |
| 9,746,432 B2 * | 8/2017 | Smith, Jr. | G01N 23/223 |
| 9,976,972 B2 * | 5/2018 | Crosby | H05G 1/02 |
| 10,018,748 B2 * | 7/2018 | Black | G01N 33/2823 |
| 10,078,060 B2 * | 9/2018 | Geier | G01T 7/00 |
| 10,155,628 B2 * | 12/2018 | Holden | B65G 43/08 |
| 10,295,486 B2 * | 5/2019 | Yun | G01N 23/223 |
| 10,641,718 B2 * | 5/2020 | Parks | G01N 23/223 |
| 10,663,415 B2 * | 5/2020 | Yoneda | G01N 23/223 |
| 10,816,488 B2 * | 10/2020 | Troadec | G01N 33/30 |
| 11,169,100 B2 * | 11/2021 | Sackett | G01N 23/223 |
| 11,199,513 B2 * | 12/2021 | Koskinen | G01N 23/223 |
| 11,360,036 B2 * | 6/2022 | Koskinen | G01N 23/223 |
| 2016/0084777 A1 | 3/2016 | Smith, Jr. et al. | |
| 2017/0167989 A1 | 6/2017 | Crosby et al. | |
| 2017/0217689 A1 | 8/2017 | Holden et al. | |

OTHER PUBLICATIONS

Application No. PCT/AU2019/050852 Written Opinion of the International Searching Authority dated Sep. 10, 2019.
Application No. PCT/AU2019/050852 International Preliminary Report on Patentability dated Jun. 26, 2020.

* cited by examiner

X-RAY FLUORESENCE APPARATUS FOR A MEASUREMENT OF MINERAL SLURRIES

RELATED APPLICATION

This application is related to Australian Provisional Patent Application No. 2018903029 titled "Apparatus for the measurement of mineral slurries" and filed 17 Aug. 2019, the entire content of which is incorporated by reference as if fully set forth herein.

TECHNICAL FIELD

The present disclosure relates to an apparatus for measuring elements within a mineral slurry. In particular, the present disclosure relates to an analyser for measuring elements within a mineral slurry by utilising X-ray fluorescence (XRF).

BACKGROUND

Ores are extracted from the earth through mining and the ores are then processed, using mineral processing, to separate commercially valuable minerals from their respective ores. Mineral processing may involve a number of different sequential steps to identify and separate various minerals from raw material extracted from a mine. Such steps depend on the particular mineral to be extracted and the mining operation, but may include, for example, crushing, vibrating, flotation, and the like.

During mineral processing, it is common to form a slurry from mixing crushed raw material with water, as slurries are a convenient way by which to transport and handle bulk materials.

At the beginning of a mineral processing arrangement, it is important to identify the amount of various elements in the slurry to be processed. After the slurry has been processed and the valuable mineral content has been extracted, the waste product is known as tailings. It is important to identify the amount of elements remaining in the slurry tailings, so that the efficiency of the mineral processing can be assessed.

Thus, a need exists to provide an improved apparatus for measuring elements in a mineral slurry.

SUMMARY

The present disclosure relates to an analyser for the measurement of elements in a mineral slurry using XRF.

A first aspect of the present disclosure provides a measurement probe for measurement of elements in a mineral slurry, said probe comprising:
a housing having an X-ray window, the housing enclosing:
an electrically powered X-ray source positioned to emit source X-rays at the X-ray window;
an X-ray detector positioned to detect X-rays from the X-ray window; and
a control module configured to:
control operation of the X-ray source and the X-ray detector;
process X-rays detected by the X-ray detector to generate X-ray spectra data; and
process said X-ray spectra data to determine the quantity of one or more elements of interest in the mineral slurry; and
a probe mount located on an outer surface of the housing and surrounding the X-ray window, the probe mount being adapted to couple the measurement probe to a pipe mount on a pipe carrying the mineral slurry, such that when the probe mount is coupled to the pipe mount the X-ray window provides a transmission window for X-rays into a lumen of the pipe.

A second aspect of the present disclosure provides an analyser for measurement of elements in a mineral slurry, the analyser comprising:
a pipe mount on a pipe carrying the mineral slurry;
a power cabinet configured to receive mains power and output low voltage power;
a measurement probe for measurement of elements in a mineral slurry, the probe including:
a housing having an X-ray window, the housing enclosing:
an electrically powered X-ray source positioned to emit source X-rays at the X-ray window;
an X-ray detector positioned to detect X-rays from the X-ray window; and
a control module configured to control operation of the X-ray source and the X-ray detector and to process X-rays detected by the X-ray detector to determine the quantity of one or more elements of interest in the mineral slurry based on X-ray spectra data derived from said processed X-rays; and
a probe mount located on an outer surface of the housing and surrounding the X-ray window, the probe mount being adapted to couple the measurement probe to the pipe mount on the pipe, such that when the probe mount is coupled to the pipe mount the X-ray window provides a transmission window for X-rays into a lumen of the pipe;
wherein the power cabinet is coupled to the measurement probe to power the measurement probe.

A third aspect of the present disclosure provides a measurement probe for measurement of elements in a mineral slurry, said probe comprising:
a housing having an X-ray window, said housing enclosing:
an electrically powered X-ray source positioned to emit source X-rays at said X-ray window;
an X-ray detector positioned to detect X-rays from said X-ray window; and
a control module configured to:
control operation of said X-ray source and said X-ray detector;
process X-rays detected by the said X-ray detector to generate X-ray spectra data; and
process said X-ray spectra data to determine the quantity of one or more elements of interest in the mineral slurry
a probe mount located on an outer surface of said housing and surrounding said X ray window, said probe mount being adapted to couple said measurement probe to a vessel mount on a vessel containing said mineral slurry, such that when said probe mount is coupled to said vessel mount the X-ray window provides a transmission window for X-rays into an interior of said vessel.

According to another aspect, the present disclosure provides an apparatus for implementing any one of the aforementioned methods.

According to another aspect, the present disclosure provides a computer program product including a computer readable medium having recorded thereon a computer program for implementing any one of the methods described above.

Other aspects of the present disclosure are also provided.

BRIEF DESCRIPTION OF THE DRAWINGS

One or more embodiments of the present disclosure will now be described by way of specific example(s) with reference to the accompanying drawings, in which.

Method steps or features in the accompanying drawings that have the same reference numerals are to be considered to have the same function(s) or operation(s), unless the contrary intention is expressed or implied.

DETAILED DESCRIPTION

The present disclosure provides an apparatus suitable for use in measuring elements in a mineral slurry by utilising X-ray fluorescence (XRF) analysis. The apparatus of the present disclosure is an analyser that is adapted to be positioned on a pipe containing a slurry, such that an X-ray source of the analyser is directed through an X-ray window of the analyser to be incident on the slurry within the pipe. An X-ray detector of the analyser detects scattered and emitted X-rays and the analyser processes data derived from the detected X-rays to determine the quantity of one or more elements of interest in the mineral slurry.

Figure 1:
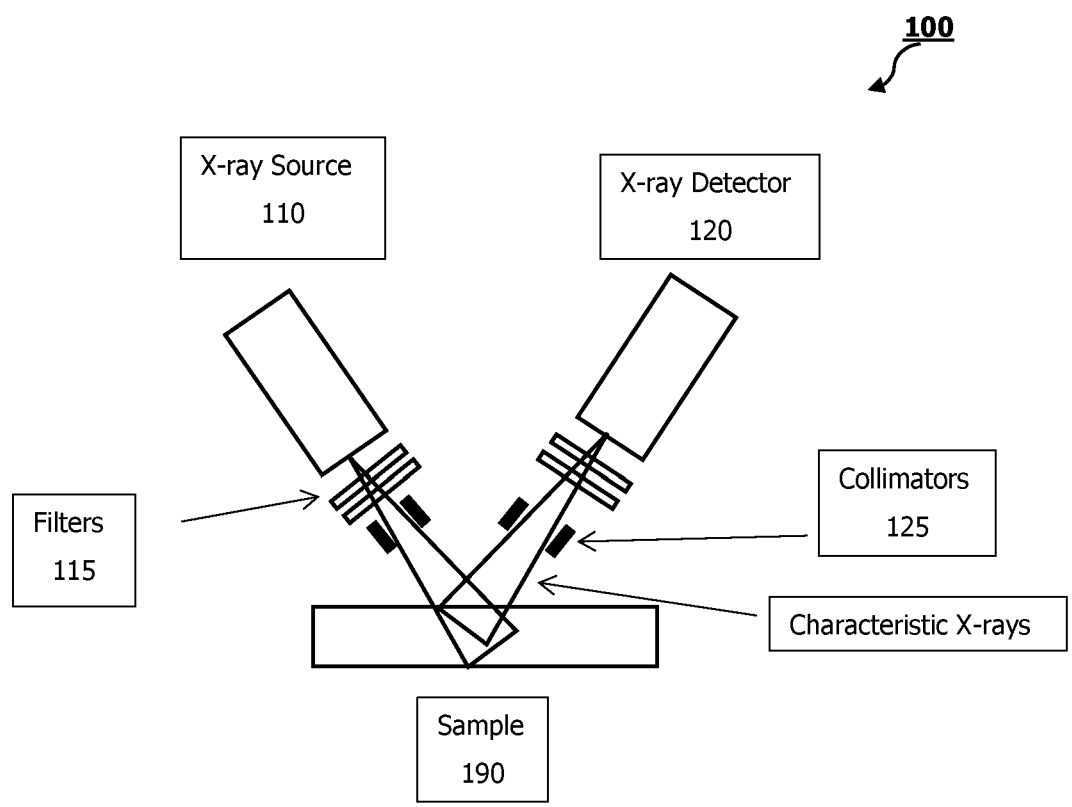
FIG. 1 is a schematic representation of an X-ray fluorescence (XRF) apparatus, suitable for use in measuring elements in a mineral slurry.

FIG. 1 is a schematic representation of an X-ray fluorescence (XRF) apparatus 100. The XRF apparatus 100 includes an X-ray source 110 that is used to generate X-rays, which are a form of electromagnetic radiation. X-rays typically have a wavelength ranging from 0.01 to 10 nanometres and energies in the range 100 eV to 100 keV. The X-ray source 110 is positioned relative to a sample 190, such that X-rays emitted from the X-ray source 110 are incidence on the sample 190.

In the example of FIG. 1, the XRF apparatus includes filters 115, which are positioned between the X-ray source 110 and the sample 190 so as to attenuate X-rays emitted from the X-ray source 110. Filtering the X-rays may be used to filter out X-rays that are not of the appropriate wavelength and/or energy for the element(s) in the sample 190 to be studied. The XRF apparatus 100 also includes an X-ray detector 120, which is adapted to receive and detect X-rays scattered from or emitted from the sample 190. Further, the XRF apparatus 100 includes collimators 125, which restrict X-rays emitted from the X-ray source 110 so that those emitted source X-rays are directed towards the sample 190, and also restricts X-rays from the sample 190 so that those emitted sample X-rays are directed towards the X-ray detector 120.

The X-ray source 110 emits X-rays directed at the sample 190. When an X-ray strikes the sample 190, the incident X-ray may be absorbed by an electron in an atom of the sample 190. If the electron is ejected during this process (known as the photoelectric effect), then a vacancy is created in an atomic orbital. When this vacancy in the atomic orbital is filled, via the transition of a higher orbital electron, the excess energy may be emitted as a characteristic X-ray whose energy is the difference between the corresponding atomic orbitals. Since each element has a unique set of orbitals, then the characteristic X-rays are unique for each element. The emitted characteristic X-rays are then received by the X-ray detector 120, which may be implemented using an Energy Dispersive detector. In particular, a Silicon Drift Detector (SDD) is particularly suitable for such an analyser. The process of measuring the emissions of characteristic X-rays and determining the elemental abundances is typically called XRF analysis.

As shown in FIG. 1, the XRF apparatus 100 includes collimators 125 and filters 115, which may be used to condition the X-rays impinging on the sample 190 and the X-ray detector 120. Differing combinations of X-ray sources 110, filters 115, collimators 125, samples 190, and X-ray detectors 120 are widely used in a variety of modern day commercial XRF instrumentation.

Figure 2:
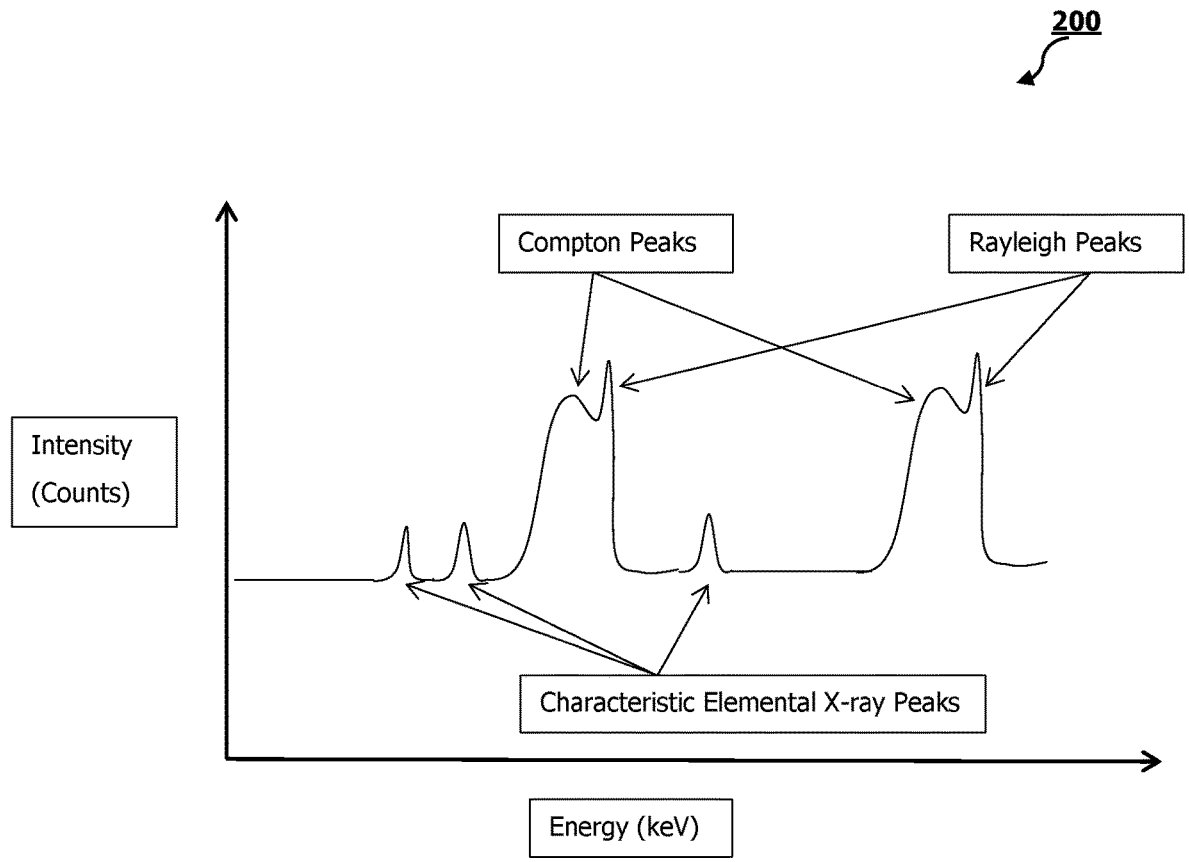
FIG. 2 is a schematic representation of a simplified XRF spectrum.

FIG. 2 shows a simplified X-ray spectrum 200 measured by an Energy Dispersive X-ray detector. The spectrum 200 consists of one or more characteristic X-ray peaks from the elements present in the sample, and additionally one or more Compton and Rayleigh peaks due the scattering of X-rays in the sample. In general, the heights of the characteristic X-ray peaks are related to their corresponding elemental abundances, whereas the Compton and Rayleigh peaks are more complexly related to the overall slurry composition.

XRF analysis techniques are particularly suitable for deployment in the mining industry, where timely characterisation of the elemental composition of a mineral slurry may result in vastly improved economics. For example, a mineral concentrator is where mineral bearing ore is processed. As part of this process, mined ore is crushed and milled, and water and chemicals are added to produce a slurry. The mineral bearing slurry is then processed via a variety of techniques, including flotation and gravity concentration, to produce a high grade slurry "concentrate", which is recovered. The waste slurry "tailings" typically exit the plant and are discarded. Timely characterisation of the slurry, via X-ray techniques, can yield much information regarding the operational state of the concentrator, resulting in much improved recovery of the valuable elements and minerals.

Figure 3:
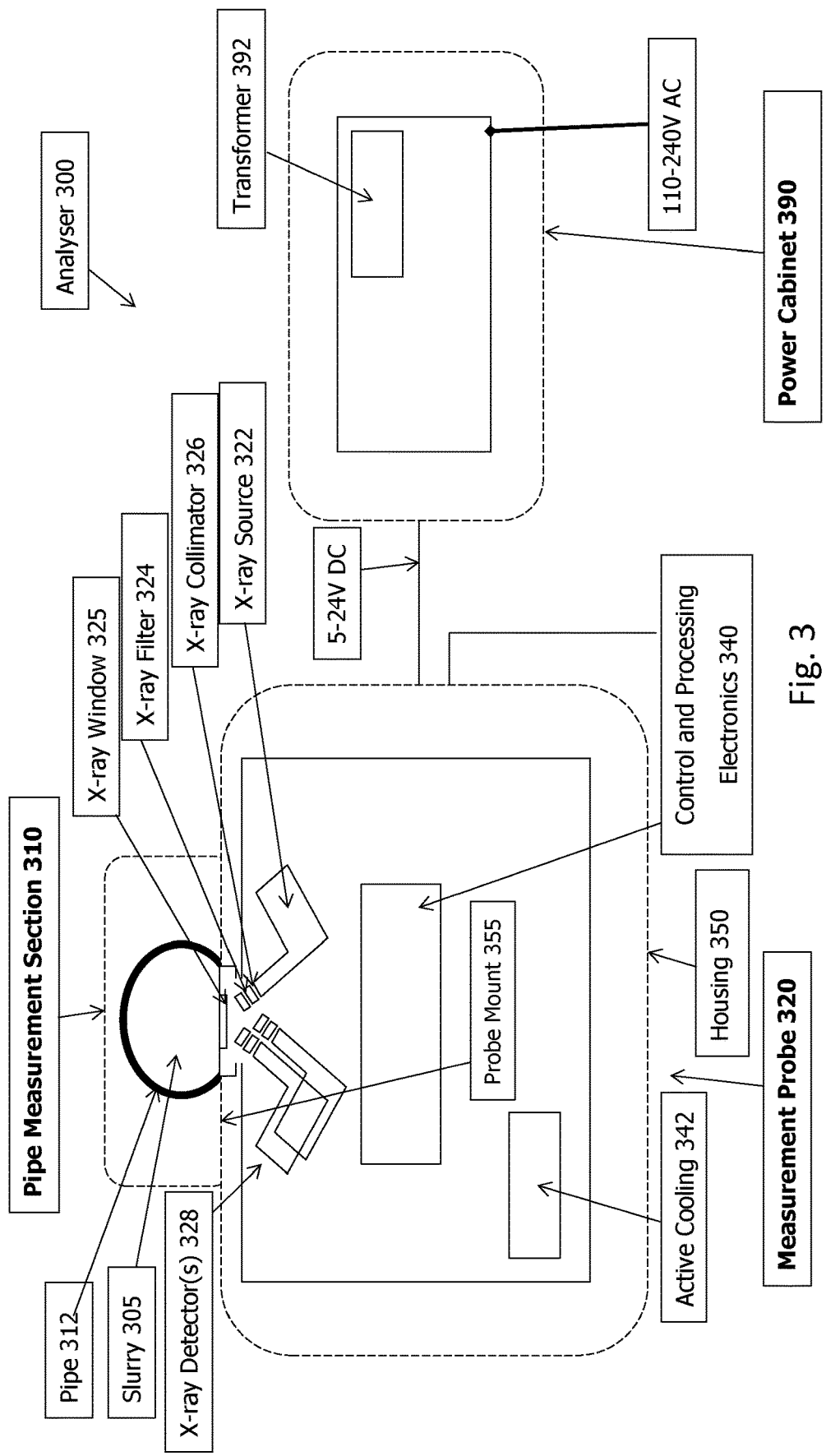
FIG. 3 is a schematic representation of an apparatus for measurement of elements in a mineral slurry.

FIG. 3 is a schematic representation of an analyser 300 for measurement of the composition of a mineral slurry 305, particularly in relation to the measurement of elements in the mineral slurry. The analyser 300 includes three components:
1. a pipe measurement section 310;
2. a measurement probe 320; and
3. a power cabinet 390.

The pipe measurement section 310 consists of a section of pipe 312 which transports the slurry and facilitates the mounting of the measurement probe 320. The pipe measurement section 310 includes an aperture to a lumen of the pipe 312, wherein the aperture is surrounded by a pipe mount adapted to couple the measurement probe 320 to the pipe 312.

The pipe mount may be implemented in many ways, including, for example, but not limited to, a flange adapted to couple to a matching probe mount 355 on the measurement probe 320. The pipe mount may optionally be secured to the probe mount 355 by one or more fasteners, wherein the fasteners may include, but are not limited to screws, bolts, threaded screw mounts, dowels, clamps, and the like, or any combination thereof. Embodiments may include a seal between the pipe mount and the probe mount 355, such as an O-ring or the like, to prevent leakage of the mineral slurry through the coupling.

In the example of FIG. 3, the measurement probe 320 includes a housing 350 for enclosing components of the measurement probe 320. The housing 350 includes a slurry window 325 made from material of sufficiently low atomic number and thickness to allow transmission of X-rays of interest into the lumen of the pipe 312. The slurry window 325 may be implemented using a material having a low atomic number (Z<15 and in some embodiments Z<10), including, but not limited to, Poly Ether Ether Ketone (PEEK), boron carbide ($B_4C$), polyester (Mylar), polycarbonate, polyamide (Nylon), polytetrafluoroethylene PTFE (Teflon), polystyrene, polyvinylchloride (PVC), magnesium alloy, aluminium alloy, quartz, or fused silica. In one or more embodiments, the slurry window 325 is implemented using multi-layered windows to provide protection for the equipment, in the case of a window failure.

The slurry window 325 is surrounded by the probe mount, such that when the pipe mount is coupled to the probe mount, the slurry window 325 is positioned to provide a transmission window for X-rays to pass between the measurement probe 320 and the lumen of pipe 312.

The housing of the measurement probe 320 encloses: X-ray source(s) 322 positioned to emit X-rays towards the slurry window 325; X-ray filter(s) 324 and collimator(s) 326 to condition the X-rays; X-ray detector(s) 328 to measure the X-rays from the direction of the slurry window 325; control and processing electronics 340 and associated software which control the analyser and process the X-ray spectrum to yield compositional information regarding the slurry; and active cooling 342 to control the temperature inside the measurement probe 320.

Various combinations of filters 324 and collimators 326 may be positioned in relation to either one or both of the X-ray source 322 and X-ray detector 328 so as to condition X-rays emitted from the source 322 and detected by the detector 328. For example, particular filters 324 may be used when measuring a certain element, in order to increase the signal to noise ratio.

The control and processing electronics 340 may be implemented using a computing device, alone or in combination with other electrical components. Such electronic components may include, for example, a transceiver for communications with an external device, a display, a speaker for audible alerts, mechanical or electrical interlocks, one or more lights (such as LEDs) to act as status indicators, and the like.

The control and processing electronics 340 stores computer program instructions that when executed on a processor are adapted to: control operation of the X-ray source 322, including turning off and on, and setting the voltage and power; control operation of the X-ray detector 328, including turning off and on, and collecting x-ray spectra (i.e, FIG. 2); and perform analysis of X-ray spectra to determine elemental abundances in the mineral slurry that is being analysed.

The measurement probe 320 may optionally include a transceiver (not shown) for remote communications facilities to allow upload/download of data. Such remote communications may be implemented using wired and/or wireless communications, including, for example, but not limited to, Ethernet, ADSL, optical fibre, 3G/4G/5G wireless mobile technologies, LoRa, Zigbee, Sigfox, Bluetooth, WiFi, and any combination thereof. In one implementation, the measurement probe 320 includes a wireless transceiver (such as a Bluetooth or WiFi transceiver) for local wireless communications with a mobile computing device, such as a tablet, phablet, laptop, or smartphone.

One embodiment of the measurement probe 320 uses a Moxtek X-ray source operating at 50 kV and a source collimator to restrict X-rays emitted from the X-ray source 322 so that the emitted X-rays impinge only on the slurry window 325. This embodiment also uses a source filter to maximise the relative intensity of 35 keV X-rays, an Amptek Silicon Drift Detector (SDD) to detect X-rays emitted from the slurry within the pipe 312, and a Detector Collimator to ensure that the vast majority of detected X-rays originate from the direction of the slurry window 325. The X-ray source 322 and X-ray detector 328 are arranged so the axial angle of the X-ray source tube 322 is equal to the axial angle of detection of the detector 328, with respect to the slurry window 325.

In one arrangement, active cooling is achieved through the use of Peltier cooling. Efficient heat transfer is achieved through the utilisation of a set of closely coupled fans on the Peltier surface. Insulation on the internal surface of the housing of the measurement probe 320 helps to achieve efficient cooling. A thermostat is optionally utilised to ensure that stable temperatures are achieved and maintained.

The measurement probe 320 is powered by the power cabinet 390. In the example of FIG. 3, the power cabinet 390 is configured to receive AC mains power, such as in the range of 110-240V AC. A transformer 392 and other electrical circuitry (not shown), such as a rectifier, convert the AC mains power to a low voltage output power supply to power the measurement probe 320. The power cabinet 390 may optionally provide a set of one or more power outlets for general use, wherein the power outlets may provide power at mains voltage, low voltage, or any other voltage value.

In the example of FIG. 3, the low voltage output power supply is in the range of 5 to 24V and is coupled to the measurement probe 320 via an outlet using a user-friendly detachable coupling that is readily used by an operator to connect and disconnect the power cabinet 390 to and from the measurement probe 320 as desired. The power cabinet 390 may also optionally be actively cooled. Depending on the implementation, the outlet may connect power and communications between the measurement probe 320 and the power cabinet 390. The outlet may be implemented using a single connector or multiple connectors, depending on the particular application.

In one arrangement, the power cabinet 390 outlet provides wired communications to an internal communications module in the measurement probe 320. The internal communications module may be part of the control and processing electronics module 340 or may be implemented using a separate transceiver.

In one example, an analyser in accordance with the present disclosure is utilised to measure palladium (Pd) content within a slurry. Software running on the control and processing electronics module 340 receives data derived from X-rays detected by the X-ray detector 328, the data forming X-ray spectra corresponding to the quantity of elements present in the mineral slurry. Irradiation of a palladium bearing slurry results in a characteristic Pd X-ray peak detected at 21.177 keV. After processing by the control and processing electronics module 340, consisting of steps including normalisation and correction for attenuation effects, the Pd composition of the slurry is calculated.

In one implementation, two analysers are utilised in a mining concentrator. A first analyser is attached to a first pipe carrying feed slurry and a second analyser is attached to a second pipe carrying tailings after mineral content has been extracted from the feed slurry. The first and second analysers are used to measure feed and tailings grade continuously, and hence determine mineral recovery in real time.

Other embodiments may utilise an X-ray source operating at higher or lower target voltages. Similarly, the X-ray detector may be oriented at greater or lesser angles than the X-ray source, dependent on the operating voltage, collimators, filters, and targeted accuracies for a given slurry measurement application.

Other embodiments may utilise multiple X-ray sources, operating at the same or different voltages and powers, with the same or different filters and collimators.

Other embodiments may utilise multiple detectors, with the same or different filters and collimators.

Other embodiments may utilise multiple X-ray sources and detectors, with the same or different filters and collimators.

Whilst XRF instrumentation has been used to make measurements on pipes, the analyser of the present disclosure is different, since it contains the processing electronics (including computer and spectral analysis software) and any other (optional) components such as remote communications and Bluetooth connectivity in the measurement probe, and is directly mounted onto the pipe. This has the advantage of ensuring that when the measurement probe leaves the factory, it will have the correct calibration for its particular X-ray source(s), detector(s), filter(s), collimator(s) and any other small changes in geometry typically seen across multiple instances of the same analyser design.

The incorporation of active cooling, such as Peltier, to control the temperature inside the measurement probe ensures increased reliability. This is particularly important for mining sites located in remoted areas, where the maximum possible reliability is of great value. The increased cost and complexity of active cooling is more than offset by the advantages of improved reliability.

The incorporation of low atomic number (Z<15 and in some embodiments Z<10) X-ray windows in the measurement probe allows the measurement of base metals and other elements that emit characteristic X-rays less than approximately 15 keV. Such low energy characteristic X-rays are unable to penetrate higher atomic number windows, especially in a mineral processing environment, where slurry pressures as great as 10 atm are expected, and hence necessitate the use of sufficiently thick windows to withstand the pressure. Depending on the application, the window thickness may be, for example, in the order of approximately 1 mm to 5 mm, but the actual thickness will depend on the rated pressure required for the pipe and the particular materials used. Examples of suitable windows include PEEK (Poly Ether Ether Ketone), boron carbide ($B_4C$), polyester (Mylar), polycarbonate, polyamide (Nylon), polytetrafluoroethylene PTFE (Teflon), polystyrene, polyvinylchloride (PVC), magnesium alloy, aluminium alloy, quartz, fused silica, or similar low atomic number materials. As indicated with reference to FIG. 3, the X-ray windows may be implemented using multi-layered windows to provide protection for the equipment, in the case of a window failure.

Other embodiments may use higher atomic number windows if the measurement of characteristic X-rays less than approximately 15 keV is not desirable.

Figure 4:
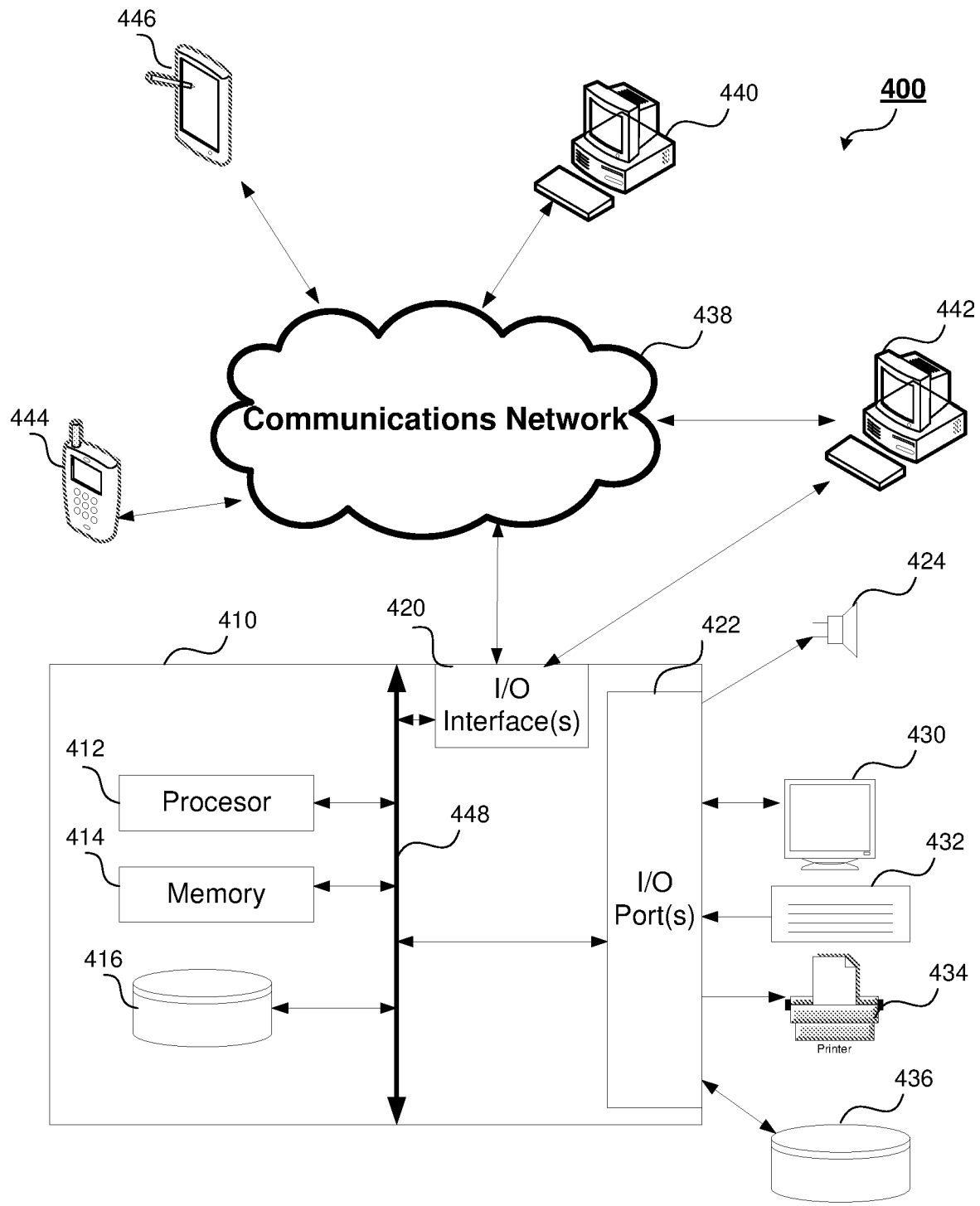
FIG. 4 is a schematic block diagram representation of a system that includes a general-purpose computer on which one or more embodiments of the present disclosure may be practised.

The control and processing electronics module 340 of the measurement probe 320 may be practised using a computing device, such as a general-purpose computer or computer server. FIG. 4 is a schematic block diagram of a system 400 that includes a general-purpose computer 410. The general-purpose computer 410 includes a plurality of components, including: a processor 412, a memory 414, a storage medium 416, input/output (I/O) interfaces 420, and input/output (I/O) ports 422. Components of the general-purpose computer 410 generally communicate using one or more buses 448.

The memory 414 may be implemented using Random Access Memory (RAM), Read Only Memory (ROM), or a combination thereof. The storage medium 416 may be implemented as one or more of a hard disk drive, a solid state "flash" drive, an optical disk drive, or other storage means. The storage medium 416 may be utilised to store one or more computer programs, including an operating system, software applications, communications protocols for mining concentrator data systems, and data. In one mode of operation, instructions from one or more computer programs stored in the storage medium 416 are loaded into the memory 414 via the bus 448. Instructions loaded into the memory 414 are then made available via the bus 448 or other means for execution by the processor 412 to implement a mode of operation in accordance with the executed instructions.

One or more peripheral devices may be coupled to the general-purpose computer 410 via the I/O ports 422. In the example of FIG. 4, the general-purpose computer 410 is coupled to each of a speaker 424, a display device 430, an input device 432, a printer 434, and an external storage medium 436. The speaker 424 may be implemented using one or more speakers, and may function to provide audible alerts in relation to the analyser. In the example in which the general-purpose computer 410 is utilised to implement the control and processing module 340 of the measurement probe 320 of FIG. 3, one or more peripheral devices may relate to a speaker or external display screen connected to the I/O ports 422.

The display device 430 may be a computer monitor, such as a cathode ray tube screen, plasma screen, or liquid crystal display (LCD) screen. The display 430 may receive information from the computer 410 in a conventional manner, wherein the information is presented on the display device 430 for viewing by a user. The display device 430 may optionally be implemented using a touch screen to enable a user to provide input to the general-purpose computer 410. The touch screen may be, for example, a capacitive touch screen, a resistive touchscreen, a surface acoustic wave touchscreen, or the like. For example, the display screen may be an LCD screen located on an external surface of the housing of the measurement probe 320 for displaying a status of the probe 320, operating parameters of the probe 320, and composition data relating to X-ray spectra of mineral slurry in the pipe 312.

The input device 432 may be a keyboard, a mouse, a stylus, drawing tablet, touchscreen, or any combination thereof, for receiving input from a user.

The I/O interfaces 420 facilitate the exchange of information between the general-purpose computing device 410 and other computing devices. The I/O interfaces may be implemented using an internal or external modem, an Ethernet connection, or the like, to enable coupling to a transmission medium. In the example of FIG. 4, the I/O interfaces 422 are coupled to a communications network 438 and directly to a computing device 442. The computing device 442 is shown as a personal computer, but may be equally be practised using a smartphone, laptop, or a tablet device. Direct communication between the general-purpose computer 410 and the computing device 442 may be implemented using a wireless or wired transmission link. Such a wired or wireless transmission link may be used, for example, to enable a technician or plant operator to monitor data relating to performance of the measurement probe 320 itself or the composition of slurry in the pipe 312.

The communications network 438 may be implemented using one or more wired or wireless transmission links and may include, for example, a dedicated communications link, a local area network (LAN), a wide area network (WAN), the Internet, a telecommunications network, or any combination thereof. A telecommunications network may include, but is not limited to, a telephony network, such as a Public Switch Telephony Network (PSTN), a mobile telephone cellular network, a short message service (SMS) network, or any combination thereof. The general-purpose computer 410 is able to communicate via the communications network 438 to other computing devices connected to the communications network 438, such as the mobile telephone handset 444, the touchscreen smartphone 446, the personal computer 440, the cloud, and the computing device 442.

One or more instances of the general-purpose computer 410 may be utilised to implement a control and processing electronics module 340 to implement a measurement probe in accordance with the present disclosure. In such an embodiment, the memory 414 and storage 416 are utilised to store data relating to X-ray spectra derived from measurement of mineral slurries in the pipe 312. Software for implementing the mineral slurry analysis system is stored in one or both of the memory 414 and storage 416 for execution on the processor 412. The software includes computer program code for implementing method steps to control operation of the X-ray source 322 and X-ray detector 328, as well as performing analysis of X-ray spectra to determine slurry composition.

Whilst the embodiment described above refer to analysing mineral slurry in a pipe, a measurement probe in accordance with the present disclosure is suitable for use in detecting the quantity of one or more elements of interest in any vessel containing a slurry, such as a stirred slurry tank. Such a measurement probe may utilise the probe mount described above to secure the measurement probe to a vessel mount on the vessel, wherein the vessel mount is similar to the pipe mount describe above.

INDUSTRIAL APPLICABILITY

The arrangements described are applicable to the mining and mineral processing industries.

The foregoing describes only some embodiments of the present invention, and modifications and/or changes can be made thereto without departing from the scope and spirit of the invention, the embodiments being illustrative and not restrictive. Although the invention has been described with reference to specific examples, it will be appreciated by those skilled in the art that the invention may be embodied in many other forms.

In the context of this specification, the word "comprising" and its associated grammatical constructions mean "including principally but not necessarily solely" or "having" or "including", and not "consisting only of". Variations of the word "comprising", such as "comprise" and "comprises" have correspondingly varied meanings.

As used throughout this specification, unless otherwise specified, the use of ordinal adjectives "first", "second", "third", "fourth", etc., to describe common or related objects, indicates that reference is being made to different instances of those common or related objects, and is not intended to imply that the objects so described must be provided or positioned in a given order or sequence, either temporally, spatially, in ranking, or in any other manner.

We claim:

1. A measurement probe for a measurement of elements in a mineral slurry, the measurement probe comprising:
   a housing having an X-ray window, the housing enclosing:
      an electrically powered X-ray source positioned to emit source X-rays at the X-ray window;
      an X-ray detector positioned to detect X-rays received through the X-ray window; and
      control and processing electronics configured to:
         control an operation of the electrically powered X-ray source and the X-ray detector;
         process X-rays detected by the X-ray detector to generate X-ray spectra data; and
         process the X-ray spectra data to determine a quantity of one or more elements of interest in the mineral slurry; and
   a probe mount located on an outer surface of the housing and surrounding the X-ray window, the probe mount being adapted to couple the housing to a pipe mount on a pipe carrying the mineral slurry, such that when the probe mount is coupled to the pipe mount, the X-ray window provides a transmission window for X-rays into a lumen of the pipe.

2. The measurement probe according to claim 1, further comprising:
   at least one Peltier device to control a temperature inside the housing.

3. The measurement probe according to claim 1, further comprising:
   a set of filters located to condition source X-rays emitted from the electrically powered X-ray source or located to condition X-rays received through the X-ray window.

4. The measurement probe according to claim 1, further comprising:
   a set of collimators located to condition source X-rays emitted from the electrically powered X-ray source or condition X-rays received through the X-ray window.

5. The measurement probe according to claim 1, further comprising:
   a low voltage power supply.

6. The measurement probe according to claim 1, wherein the X-ray window comprises a low atomic number material.

7. The measurement probe according to claim 6, wherein the X-ray window is a multi-layered window.

8. The measurement probe according to claim 1, further comprising:
   an outlet for releasably coupling the housing to a power cabinet providing a power supply.

9. The measurement probe according to claim 8, wherein the outlet includes a communications interface for exchanging slurry composition data with the power cabinet.

10. The measurement probe according to claim 8, wherein the power cabinet receives input mains power and outputs a low voltage direct current (DC) power to the measurement probe via the outlet.

11. The measurement probe according to claim 1, wherein the control and processing electronics is further configured to output slurry composition data.

12. The measurement probe according to claim 1, further comprising a plurality of X-ray detectors positioned to detect X-rays received through the X-ray window.

13. A measurement probe for a measurement of elements in a mineral slurry, the measurement probe comprising:

a housing having an X-ray window, the housing enclosing:
  an X-ray source positioned to emit source X-rays at the X-ray window;
  an X-ray detector positioned to detect X-rays received through the X-ray window; and
  control and processing electronics configured to:
    control an operation of the X-ray source and the X-ray detector;
    process X-rays detected by the X-ray detector to generate X-ray spectra data; and
    process the X-ray spectra data to determine a quantity of one or more elements of interest in the mineral slurry; and
a probe mount located on an outer surface of the housing and surrounding the X-ray window, the probe mount being adapted to couple the housing to a vessel mount on a vessel containing the mineral slurry, such that when the probe mount is coupled to the vessel mount, the X-ray window provides a transmission window for X-rays into an interior of the vessel.

14. The measurement probe according to claim 13, wherein the probe mount is adapted to couple the housing to a tank containing the mineral slurry.

15. An analyser for a measurement of elements in a mineral slurry, the analyser comprising:
a pipe mount on a pipe carrying the mineral slurry;
a power cabinet configured to receive mains power and output low voltage power; and
a measurement probe for a measurement of elements in a mineral slurry, the measurement probe including:
a housing having an X-ray window, the housing enclosing:
  an X-ray source positioned to emit source X-rays at the X-ray window;
  an X-ray detector positioned to detect X-rays received through the X-ray window; and
  control and processing electronics configured to:
    control an operation of the X-ray source and the X-ray detector;
    process X-rays detected by the X-ray detector to generate X-ray spectra data; and
    process the X-ray spectra data to determine a quantity of one or more elements of interest in the mineral slurry; and
a probe mount located on an outer surface of the housing and surrounding the X-ray window, the probe mount being adapted to couple the measurement probe to the pipe mount on the pipe, such that when the probe mount is coupled to the pipe mount, the X-ray window provides a transmission window for X-rays into a lumen of the pipe;
wherein the power cabinet is coupled to the measurement probe to power the measurement probe.

* * * * *